(12) United States Patent
Barak et al.

(10) Patent No.: US 10,365,163 B2
(45) Date of Patent: *Jul. 30, 2019

(54) OPTICAL CRITICAL DIMENSION METROLOGY

(71) Applicant: NOVA MEASURING INSTRUMENTS LTD., Rehovot (IL)

(72) Inventors: Gilad Barak, Rehovot (IL); Dror Shafir, Kiryat Ono (IL); Danny Grossman, Herzliya (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/053,210

(22) Filed: Aug. 2, 2018

(65) Prior Publication Data

US 2019/0063999 A1 Feb. 28, 2019

Related U.S. Application Data

(63) Continuation of application No. 15/120,847, filed as application No. PCT/IL2015/050203 on Feb. 23, 2015, now Pat. No. 10,041,838.

(Continued)

(51) Int. Cl.
*G01J 9/00* (2006.01)
*G01J 9/02* (2006.01)
(Continued)

(52) U.S. Cl.
CPC ............... *G01J 9/00* (2013.01); *G01B 11/02* (2013.01); *G01J 9/02* (2013.01); *G01N 21/21* (2013.01);
(Continued)

(58) Field of Classification Search
CPC ..... G01J 9/00; G01J 9/02; G01B 11/02; G01N 21/21; G01N 21/9501; G01N 21/956; G01N 2210/56; G01N 2201/12
(Continued)

(56) References Cited

U.S. PATENT DOCUMENTS 8,848,185 B2 9/2014 Barak et al.
2003/0144819 A1 7/2003 Takeuchi et al.
(Continued)

FOREIGN PATENT DOCUMENTS

WO 2014/102792 7/2014
WO 2014/128710 8/2014

OTHER PUBLICATIONS

Edited by Y.C. Eldar and G. Kutyniok, Compressed Sensing, Theory and Applications, Cambridge University Press, 2012, pp. 1-544.
(Continued)

*Primary Examiner* — Hina F Ayub
(74) *Attorney, Agent, or Firm* — Browdy and Neimark, P.L.L.C.

(57) ABSTRACT

A metrology system is presented for measuring parameters of a structure. The system comprises: an optical system and a control unit. The optical system is configured for detecting light reflection of incident radiation from the structure and generating measured data indicative of angular phase of the detected light components corresponding to reflections of illuminating light components having different angles of incidence. The control unit is configured for receiving and processing the measured data and generating a corresponding phase map indicative of the phase variation along at least two dimensions, and analyzing the phase map using modeled data for determining one or more parameters of the structure.

20 Claims, 6 Drawing Sheets

Related U.S. Application Data

(60) Provisional application No. 61/943,389, filed on Feb. 23, 2014.

(51) Int. Cl.
  G01B 11/02 (2006.01)
  G01N 21/956 (2006.01)
  G01N 21/95 (2006.01)
  G01N 21/21 (2006.01)

(52) U.S. Cl.
  CPC ....... G01N 21/9501 (2013.01); G01N 21/956 (2013.01); *G01B 2210/56* (2013.01); *G01N 2201/12* (2013.01)

(58) Field of Classification Search
  USPC ........................................................ 356/364
  See application file for complete search history.

(56) References Cited

U.S. PATENT DOCUMENTS

| | | |
|---|---|---|
| 2004/0085544 A1 | 5/2004 | De Groot |
| 2005/0018183 A1 | 1/2005 | Shortt |
| 2007/0091320 A1 | 4/2007 | Hu et al. |
| 2012/0008147 A1* | 1/2012 | Finarov ............... G01B 11/24 356/601 |
| 2012/0323356 A1* | 12/2012 | Dziura ............... G01N 21/47 700/121 |
| 2014/0168646 A1 | 6/2014 | Barak et al. |

OTHER PUBLICATIONS

Velghe, et al., Wave-front reconstruction from multidirectional phase derivatives generated by multilateral shearing Interferometers, Opt. Lett., Feb. 2005, pp. 245-247, vol. 30, No. 3.

\* cited by examiner

OPTICAL CRITICAL DIMENSION METROLOGY

TECHNOLOGICAL FIELD AND BACKGROUND

The present invention is generally in the field of optical measurement techniques, and relates to a method and system for optical critical dimension (OCD) metrology, particularly useful for measuring in patterned structures, such as semiconductor wafers.

Over the last few decades, semiconductor devices become ever smaller and more elaborate, and fabrication tolerances increasingly challenging. One solution to this growing challenge is found through improved metrology capabilities, allowing better control and monitoring of the fabrication process.

One of the strongest technologies in use today for semiconductor characterization is Optical Critical Dimension (OCD) metrology. This title is in fact used to describe a set of optical techniques implementing scatterometry: measurement of light scattering properties of the sample. Through accurate numerical models, it is then possible to relate the measured scattering properties to the geometrical and material characterizations of the sample under test.

Today, optical critical dimension (OCD) metrology is largely based on spectral reflectometry (SR) and spectral ellipsometry (SE). Additional forms of metrology in use are full Mueller matrix characterization and dome scatterometry. All these techniques are based on measuring the reflected intensity of differently polarized light for different incident directions.

For example, U.S. Pat. No. 8,848,185 and US 2014/168646, both assigned to the assignee of the present application, describe an optical system for use in measuring a via profile parameters in a patterned structure.

According to U.S. Pat. No. 8,848,185, the system comprises an illumination channel for propagating illuminated light onto the structure being measured, a detection channel for collecting light returned from the illuminated structure to a detection unit, and a modulating assembly configured and operable for implementing a dark-field detection mode by carrying out at least one of the following: affecting at least one parameter of light propagating along at least one of the illumination and detection channels, and affecting propagation of light along at least the detection channel.

According to US 2014/168646, the optical system comprises an illumination channel for propagating illuminated light onto the structure being measured; a detection channel for collecting light returned from the illuminated structure to a detection unit; and an attenuation assembly accommodated in the illumination and detection channels and being configured and operable for selectively attenuating light propagating along the detection channel, the attenuation creating a predetermined condition for the selectively attenuated light, said predetermined condition being defined by a predetermined ratio between a first light portion corresponding to a dark field condition and a second light portion corresponding to a bright field condition in said selectively attenuated light, detected selectively attenuated light being therefore indicative of at least one parameter of the via being illuminated.

GENERAL DESCRIPTION

The present invention provide a novel technique for OCD measurements, which is based on measuring a relative phase between light propagating from illumination region on a sample in different directions. This technique provides a sensitive and information-rich approach for OCD. The inventors term this approach "angular phase metrology".

The present invention takes advantages of a relative phase approach in measuring in patterned structures. The relative phase is a phase shift between incident and reflected light beams. Such a phase shift is different for interactions of incident light with different regions of the structure (e.g. differently patterned regions, patterned and unpatterned regions, regions with different material layers, etc.), as well as is different for different wavelengths of incident light, and can thus present a spectral phase shift. These techniques are disclosed in WO 2014/128710 and WO 2014/102792 assigned to the assignee of the present application.

The present invention provides a novel technique, based on angular phase measurements, which can be used in measuring in multi-layer structures, such as semiconductor wafers. The technique is particularly useful for OCD measurements. The angular phase measurements of the present invention may be implemented to provide 2D information set (e.g. angular phase measurements obtained for a range of incident angles and azimuths, or over a range of incident angles and wavelengths), as well as 3D information set (e.g. the angular phase is measured over a range of incident angles, azimuths and wavelengths).

Thus, according to one broad aspect of the invention, there is provided a metrology system for measuring parameters of a structure, the system comprising: an optical system configured for detecting light reflection of incident radiation from the structure and generating measured data indicative of angular phase of the detected light components corresponding to reflections of illuminating light components having different angles of incidence; and a control unit configured for receiving and processing the measured data and generating a corresponding phase map indicative of the phase variation along at least two dimensions, and analyzing the phase map using modeled data for determining one or more parameters of the structure.

The at least two dimensions may comprise angular data on the structure along the two axis in the detection plane. In some embodiments, the at least two dimensions comprise angular data on the structure along one axis and spectral data. In some other embodiments, the at least two dimensions comprise position (angular) data on the structure along the two axis and additionally comprise spectral data.

In some embodiments, the optical system is configured and operable for illuminating the structure with one or more wavelength, and detecting the light reflection for said one or more wavelengths. In some embodiments, the optical system is configured and operable for illuminating the structure with multiple wavelength, either concurrently or sequentially.

The optical system may be configured for illuminating the sample with light of a specific polarization, and detecting reflected light of a desired polarization, e.g. orthogonal polarization.

The optical system may comprise a phase detector.

The processing of the measured data included fitting procedure between the measured data and theoretical model. Typically, the fitting process includes merit function definition. The merit function is a measure of the degree of fit between calculated and measured data. The merit function may be the RMS error between measurement and calculation data pieces, where each of the measurement and calculation data pieces is in the form of reflected intensity I and phase $\phi$ simultaneously. For example, the reflected intensity and phase may be each a function of the wavelength(s) used in the measurements, polarizations and incident\reflected angles, for a plurality of data points.

According to another aspect of the invention, there is provided a method for use in measurements of one or more parameters of a structure, the method comprising: providing measured data indicative of angular phase of light components corresponding to reflections of illuminating light components having different angles of incidence onto the structure; processing the measured data and determining a corresponding phase map indicative of the phase variation along at least two dimensions; and analyzing the phase map using modeled data for determining one or more parameters of the structure.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A shows a converging spherical wavefront of a light response of a sample; and FIGS. 1B and 1C show the behavior of the reflected wavefront for respectively a perfect mirror and a general sample;

FIGS. 4A and 4B present the results of calculated angular phase for TE and TM polarizations; and FIG. 4C presents the angular phase in a cross-polarization optical scheme, where the illumination is done at TE polarization, and only the TM polarization component of the returned light is collected for detection;

FIG. 5A shows a 2D phase map of the entire measured pupil, and FIGS. 5B and 5C show the cross sections of the measured 2D phase map along x and y axes and the theoretic (calculated) data;

DETAILED DESCRIPTION OF EMBODIMENTS

Figures 1A, 1B, 1C:
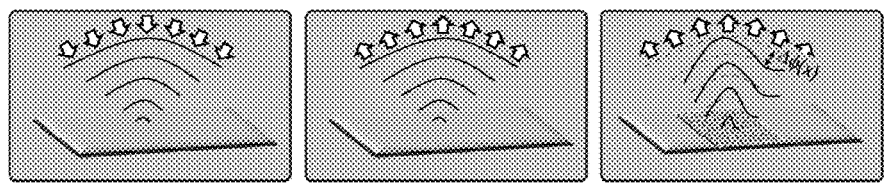
FIGS. 1A to 1C illustrate schematically the physical meaning of an angular phase measurement, where

The present invention provides a novel angular phase metrology technique for use in OCD measurements. In this connection, reference is made to FIGS. 1A to 1C which illustrate schematically the physical meaning of angular phase. FIG. 1A shows a sample and a converging spherical wavefront of light being focused on a region of the sample. As shown in FIG. 1B, if a sample is a so-called "perfect mirror", the reflected wavefront from the sample would be spherical and diverging. As shown in FIG. 1C, contrary to reflection from simple mirrors, light reflected from a general sample (which never behaves as an ideal mirror) experiences angle-dependent phase shifts (between the phases of incoming/illuminating and reflected beams), and thus the angular phase of wavefront returned from the general sample deviates from perfect spherical. While the absolute value of this phase shift is meaningless (it is changing with extremely high frequency, following the oscillating electromagnetic wave), a relative phase $\Delta\varphi$ between different reflected angles can be measured and compared.

The term "angular phase" is used here to refer to the relative phase (phase difference) between light reflected at some direction and light reflected at some (arbitrarily chosen) reference direction, e.g. a chief ray.

The angular phase depends on the nature and characteristics of the sample being measured. OCD targets (i.e. patterned structures) are commonly characterized by a set of geometrical and material-related parameters (such as critical dimensions (CD), side wall angle (SWA), thicknesses, refractive indices, etc.). For such OCD targets, it is possible to calculate the angular phase for every combination of two or more of such characteristics using standard electromagnetic calculation tools (e.g. Rigorous Coupled Wave Approximation, Finite Elements Method, Finite Difference Time Domain etc.). Hence, the measured phase distribution can be compared to a large set of precalculated results of OCD measurements. By finding the combination of parameters which produce the best fit between measured and calculated phase distribution, the actual parameters of the measured sample can be obtained.

Figure 2:
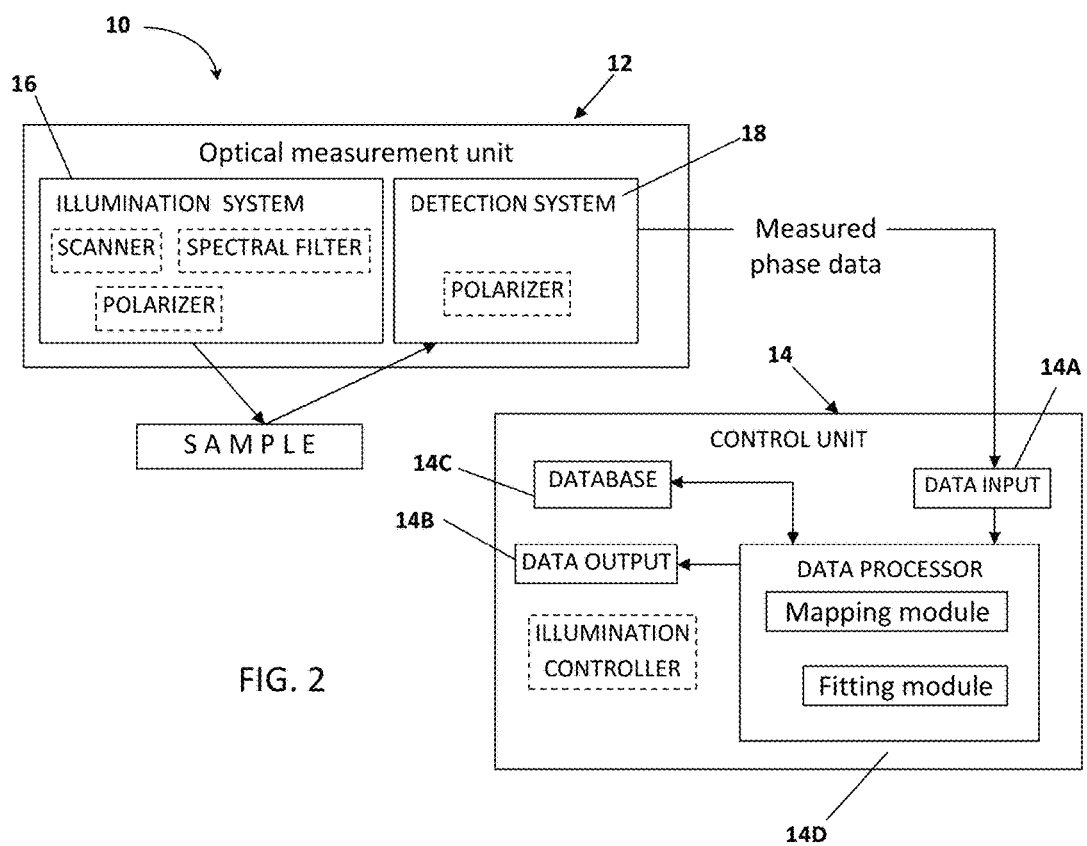
FIG. 2 schematically illustrates an optical measurement system utilizing the principles of the present invention.

Referring to FIG. 2, there is schematically illustrated an OCD measurement system 10 utilizing the principles of the present invention. The system 10 includes an optical unit 12 and a control unit 14 in data communication with the optical unit 12, via wires or wireless signal transmission using any known suitable technique. The optical unit 12 includes illumination and detection assemblies 16 and 18 configured for illuminating a sample, detecting light returned from the sample, and providing measured data indicative of the phase of the detected light. The entire measured data gathered from different locations on the sample (e.g. by scanning) provides angular phase distribution (map).

The control unit 14 is typically a computer system including inter alia data input and output utilities 14A, 14B, and a data processor 14D, and being associated with memory utility 14C which may be constituted by an external storage device (database) to which the control unit has access (e.g. via a communication network). The data processor 14D includes a mapping module configured for receiving and processing the measured data and generating a corresponding angular phase map, and a fitting module for receiving and analyzing the angular phase map to find a best fit with theoretical data stored in the memory and generate output data indicative of one or more OCD parameters corresponding to the best fit condition. Instead or in combination with usage of database (library) approach, Real Time Regression technique could be used.

As also shown in the figure, the system may be configured to scan the wafer, as well as to utilize single wavelength or multiple wavelength (e.g. controllably varying illumination wavelength). Also, the optical system may utilize polarization effects. These will be described more specifically further below.

The angular phase distribution can be measured using several techniques. These include for example the Hartmann and Shack-Hartmann sensors, phase extraction using lateral shearing interferometry (e.g. Phasics sensor [S. Velghe, J. Primot, N. Guérineau, M. Cohen and B. Wattellier, Wavefront reconstruction from multidirectional phase derivatives generated by multilateral shearing interferometers, Opt. Lett., 30 (3), p. 245-247 (2005)]), point diffraction interferometers, and pupil plane phase mapping. For the purposes of OCD, the performance requirements from these tools would be different than from their common use (e.g. characterization of optical elements).

While stress is usually put on angular resolution, for OCD the phase is typically not expected to show fast changes vs. angle and this resolution can be reduced. On the other hand, such wavefront sensors as mentioned above are not usually required to provide extremely accurate phase values. They are more often used for rough characterization of optical elements, with little significance for the absolute phase values. For the technique of the invention, required phase accuracy is relatively high, and errors are to be lower than a few percent at most.

Figure 3:
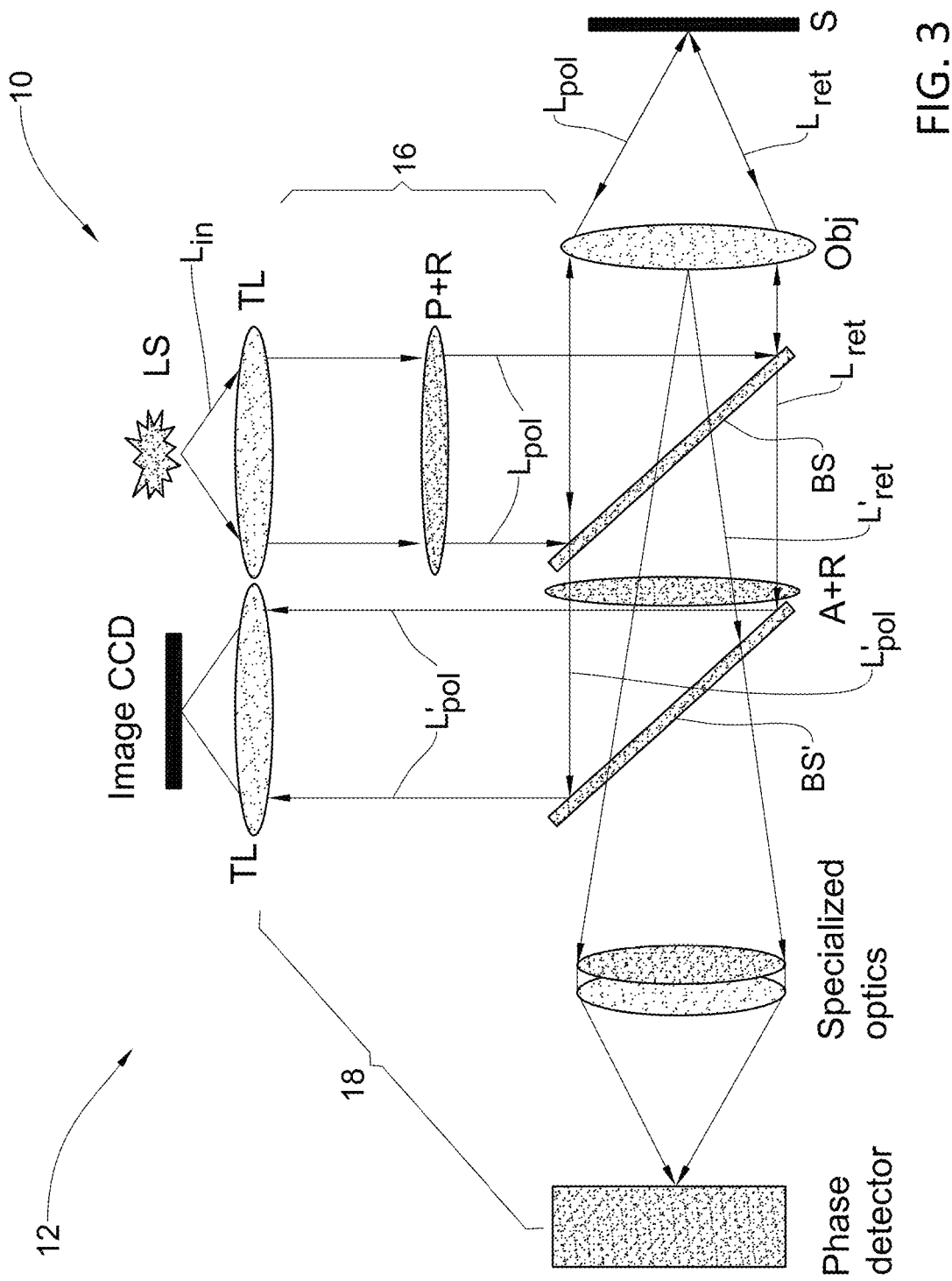
FIG. 3 shows specific but not limiting example of the configuration of the optical unit suitable to be used in the measurement system of the invention for 2D mapping of angular phase of the light response of the sample for a single wavelength.

Reference is made to FIG. 3 showing specific but not limiting example of the system of the invention. In this example, the system is configured for 2D mapping of angular phase of the light response of the sample (e.g. wafer), for a single wavelength. As in this implementation illumination is required to be monochromatic, laser illumination can be used, allowing significantly stronger illumination. The optical unit 12 includes illumination and detection assemblies 16 and 18 associated with light directing optics defining illumination and collection channels. In this scheme, input light $L_{in}$ from a light source LS is collimated by a tube lens TL and directed to a polarizer and retarder unit P+R and then to a beam splitter BS which reflects polarized light $L_{pol}$ towards an objective lens unit Obj (having one or more lenses) which focuses the polarized light beam $L_{pol}$ onto a sample S. Light $L_{ret}$ returned from the sample S is collected by the objective Obj and then passes through the beam splitter BM and an analyzer/retarder unit A+R, and so-produced polarized light $L'_{pol}$ propagates to a second beam splitter BM' which reflects this light to an imaging detector denoted here as Image CCD. The beam splitters BM and BM' pass a portion of the returned light $L'_{ret}$ to an optical scheme, specialized optics (including imaging and focusing lenses), that creates an image of the pupil on the phase detector, i.e. an instrument that measures the optical wavefront such as the above mentioned Shack-Hartmann detector. In this configuration, the illumination and detection channels have common optical elements of the light directing optics, such as objective lens unit Obj and beam splitter BS.

It should be understood that although, generally, for the purposes of the present invention, the use of a laser lightsource is not necessarily, such implementation can eliminate one of the bottlenecks of common broadband OCD methods, namely the long required acquisition times, leading to limited throughput. In addition, using laser illumination, it is possible to obtain an extremely small spot size (diffraction limited), which might be important for advanced OCD application (for example, in-die metrology, where test pads are few microns wide). It should further be noted that a set of discrete laser sources, or a broadband source and variation of spectral filtering, can be used to obtain the phase map corresponding to different wavelengths.

Additional information can be obtained when controlling the polarization in the illumination and\or detection channels. This can be accomplished by using a polarizer and\or analyzer. More extensive control on the polarization degrees of freedom can be implemented by using, in addition, a retarder in the illumination and\or detection channels.

Figure 4A:
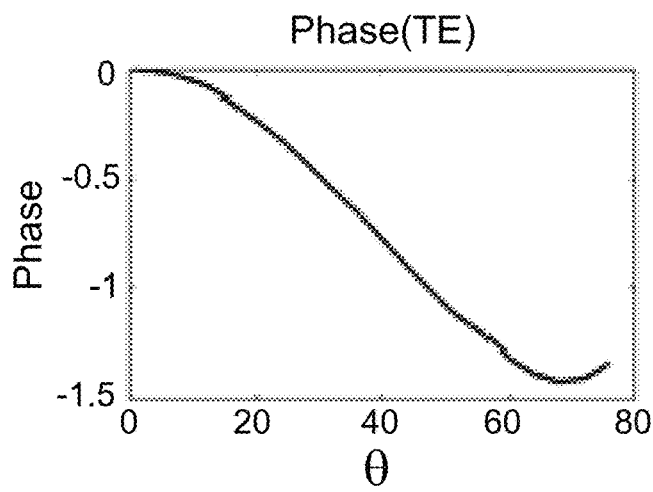
FIGS. 4A-4C exemplify calculated angular phase results for a grating application on three specific polarization schemes, where
Figure 4B:
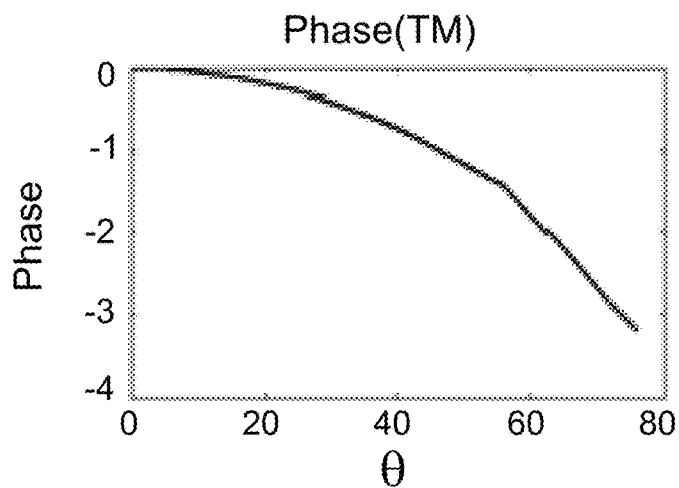
Figure 4C:
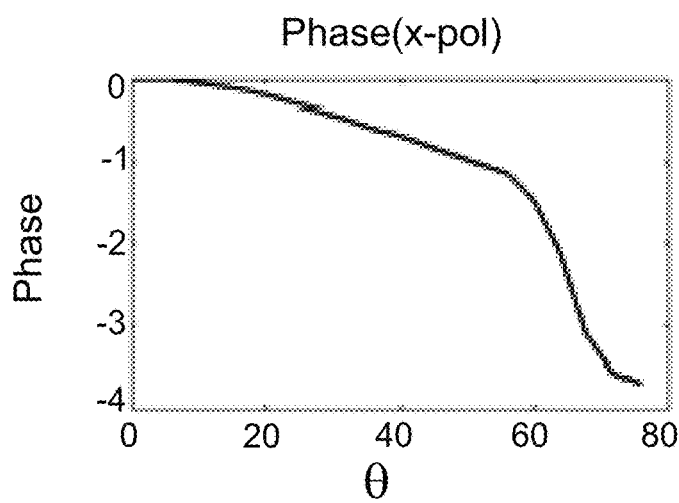

Reference is made to FIGS. 4A-4C exemplifying calculated angular phase results for a grating application on three specific polarization schemes. FIGS. 4A and 4B present the results of calculated angular phase for a grating application, for TE and TM polarizations (wavelength of 670 nm). FIG. 4C presents the angular phase in a cross-polarization optical scheme, where the illumination is done at TE polarization, and the collection analyzer is configured to collect only the TM polarization component. Using these separate channels allows better characterization of the measured sample. It should be understood that these are just few non-limiting examples of the various polarization schemes which are applicable in the technique of the invention.

Figure 5A:
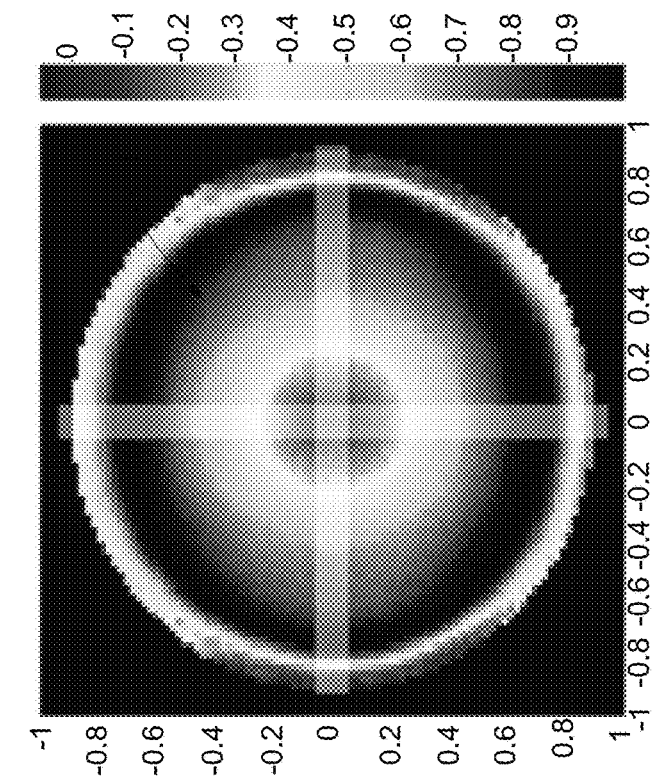
FIGS. 5A to 5C show experimental results for angular phase measurement for a relatively thick SiOx application, where
Figure 5C:
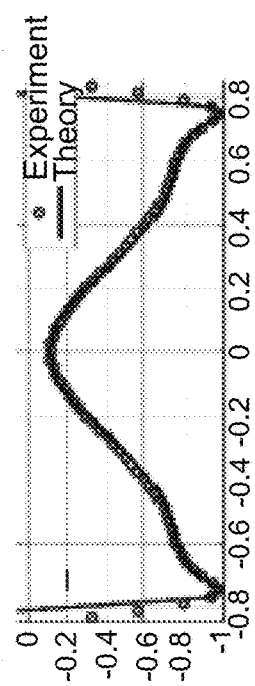
Figure 5B:
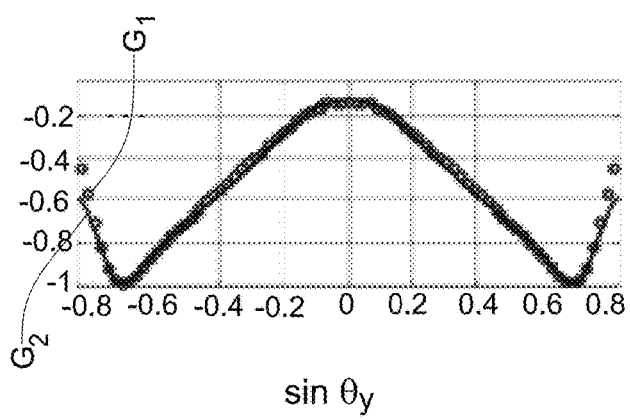

The following is the description of the experimental implementation performed by the inventors. In this experiment, the angular phase of a sample consisting of 1000 nm of SiOx on a silicon substrate was measured using the above described optical setup. Illumination was done using a Xenon lamp as a light source LS) and spectrally filtering the 550±10 nm spectral band of the Xenon lamp. The phase was measured using the Phasics phase sensor. FIGS. 5A to 5C show measured angular phase for such thick SiOx application. FIG. 5A shows a 2D phase map of the entire measured pupil (using the specialized optics with the numerical aperture (NA) of 0.85). Colors represent the reflected angular phase; and axes hold values of sin θx and sin θy. FIGS. 5B and 5C show the cross sections (dotted curve $G_1$) of the 2D phase map along x and y axes, and continuous curves show the theoretic (calculated) data. As shown, there is a good fit between the measured and theoretic data. Thus, calculation of the angular phase shows a good fit to the measured one.

Figure 6:
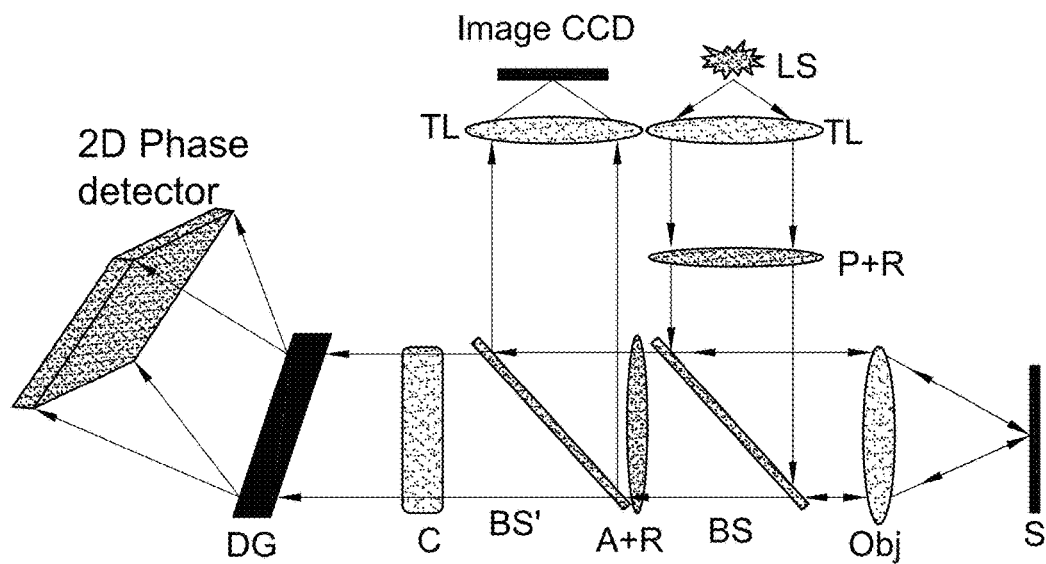
FIG. 6 shows another specific but not limiting example of the configuration of the optical unit suitable to be used in the measurement system of the invention for 2D mapping of the angular phase of the light response of a sample concurrently for multiple wavelengths.

While the full two-dimensional map of the angular phase (covering reflection vs. both angle and azimuth of incidence, such as examples depicted in FIGS. 5A-5C), holds valuable information on the measured application, it is possible to measure the phase in one direction only, and 'trade' the second direction for spectral information. In this connection, reference is made to FIG. 6, exemplifying a measurement system with the suitable optical scheme. The optical unit/ scheme in this system is generally similar to that of FIG. 3, and therefore the same reference symbols are used for identifying components that are common in both examples. Input light from a light source LS is collimated by a tube lens TL and directed to a polarizer and retarder unit P+R and then to a beam splitter BS which reflects polarized light towards an objective lens unit Obj which focuses the polarized light beam onto a sample S. Light returned from the sample S is collected by the objective Obj and then passes through the beam splitter BM and an analyzer/retarder unit A+R and so-produced polarized light propagates to a second beam splitter BM' which reflects this light to an Image CCD. The beam splitters pass a portion of the returned light to an optical scheme, including a cylindrical lens C and a diffraction grating DG, that images the pupil onto a 2D sensor. The angular phase along the directions is collected concurrently for multiple wavelengths, which are recorded on separate lines of the collection detector.

Such "trading" of dimensions vs spectral information is required in order to have simultaneous measurement on a 2D sensor. Alternatively, more comprehensive information can be obtained using a scanning system, which collects different aspects of the information consecutively. For example, the 2D phase image for all incident angles can be measured, and the illuminated wavelength scanned so that consecutive images hold the information for different wavelengths.

Figure 7:
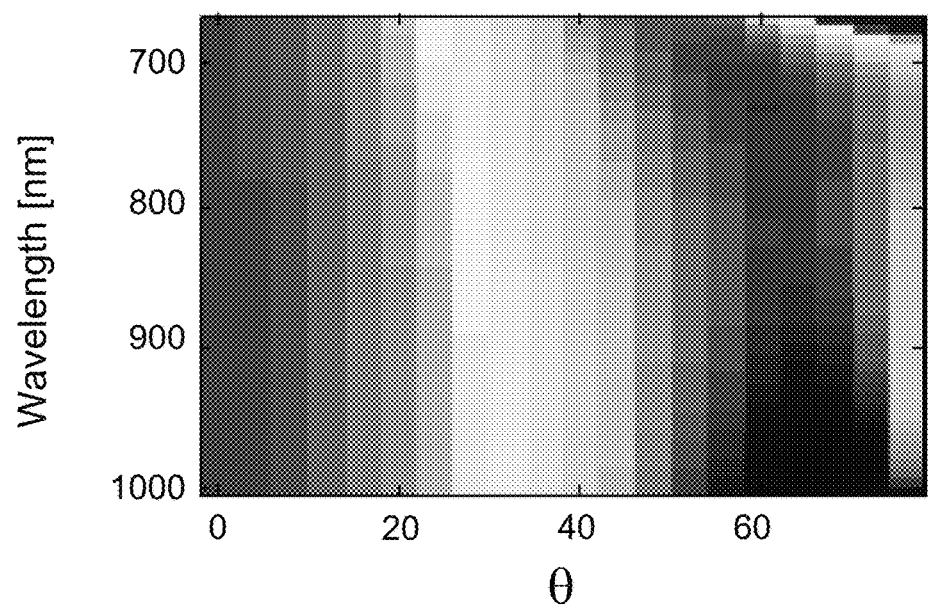
FIG. 7 exemplifies the results of calculation of the wavelength-dependent angular phase.

In one possible implementations of this scheme, light from the sample could be focused onto the phase detector using a cylindrical lens C and a diffraction grating DG. Such implementation benefits from the extensive information obtained (simultaneously) through broadband metrology, as well as the unique data obtained through angular phase. FIG. 7 presents an example of the wavelength-dependent angular phase, showing rich information. This is an example of the wavelength-dependent angular phase, calculated for a grating target with pitch of 170 nm. As can be seen, for every wavelength, a vector of phase per inclination angle can be measured.

The spectral/angular information content is generally three dimensional, namely two angular dimensions and one spectral dimension. It should be noted, that in the above example of FIG. 6, one of the angular dimensions is suppressed and a 2D information matrix (one spectral and one angular) is measured, whereas in the former example of FIG. 3 the spectral dimension is suppressed in favor of two angular axes. There are various possibilities to measure all three dimensions using a two dimensional detector utilizing a scanning mechanism. One possibility is to use a 2D angular detector and scan the wavelengths with an adjustable mono-chromator or color filter. Another option is to separate different wavelengths spatially and measure them in spatially resolved 2D angular phase detectors. A further option is to use a 2D spectral-angular detector and scan the remaining angular axis by rotating the sample.

The technique of the invention can be used in conjunction with other OCD techniques. In typical OCD applications more information collected from the sample allows for better metrology. Using different information channels allows separation between the influences of different geometrical\material parameters, and provides sensitivity to more properties of the measured sample. Several approaches have been suggested to increase the number of information channels (e.g. full Mueller matrix characterization, normal and oblique spectral reflectometry, use of dome metrology in addition to spectral reflectometry (SR) or spectral ellipsometry (SE), etc.).

Measurements of angular phase can similarly be integrated into a more comprehensive OCD metrology scheme, implementing other information channels. For example, the angular phase measurement can accompany standard SR metrology, either as an additional measurement unit, additional measurement head or even a different channel in the same metrology head. Spectral Reflectometry (SR) characterizes unknown properties of a sample by measuring the reflection of light in different wavelengths from the sample.

Specifically, a system that is designed to measure the angular intensity profile of a target (such as back focal plane imaging or Dome imaging) can be joined with a phase detector to complement the measured data with the phase information. Alternatively, a specially designed wave-front sensor (phase detector) can be used to measure the angular intensity and phase in the same time. This option includes various methods of phase and intensity characterization such as described for example in PCT/IL2013/051075, assigned to the assignee of the present application and incorporated herein by reference.

Figure 8:
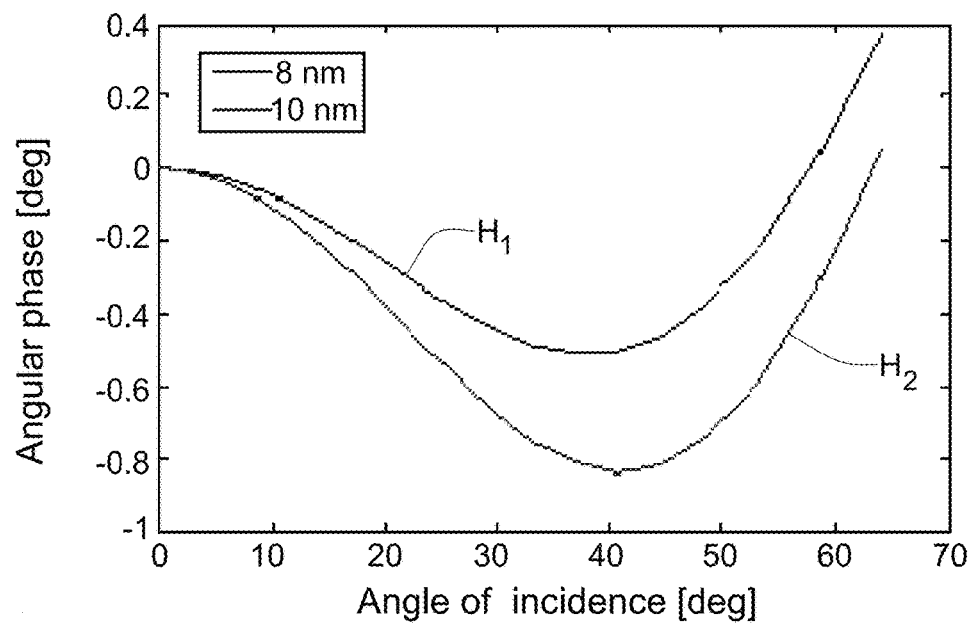
FIG. 8 demonstrates how the technique of the present invention can be used for measuring in samples with ultra-thin films, showing the measurement results for phase vs. angle of incidence for ultra-thin film.

The technique of the present invention can be used for thin-film metrology. Measurement of thin film thickness poses a significant challenge. FIG. 8 illustrates measurement results for phase vs. angle of incidence for ultra-thin film, measured by the technique of the invention using 200 nm wavelength light. Two graphs $H_1$ and $H_2$ correspond to the measurements on two samples with respectively 8 nm and 10 nm thick layers (here, layer is assumed to be SiO2 on Si. As shown, a very significant difference in signal is found, even for only 2 nm difference in the film thickness. It is thus evident that the technique of the invention (angular phase measurements) allows for extremely sensitive probe to thin films.

Superior sensitivity to thickness could be achieved using higher dimensional techniques such as described above for the spectral-angular measurement mode. Multiple wavelengths or a broadband measurement can be used, measurement of 2D (rather than 1D) angular phase can be obtained, and relative orientation of polarization in the illumination and collection can be controlled to optimize sensitivity.

Figure 9:
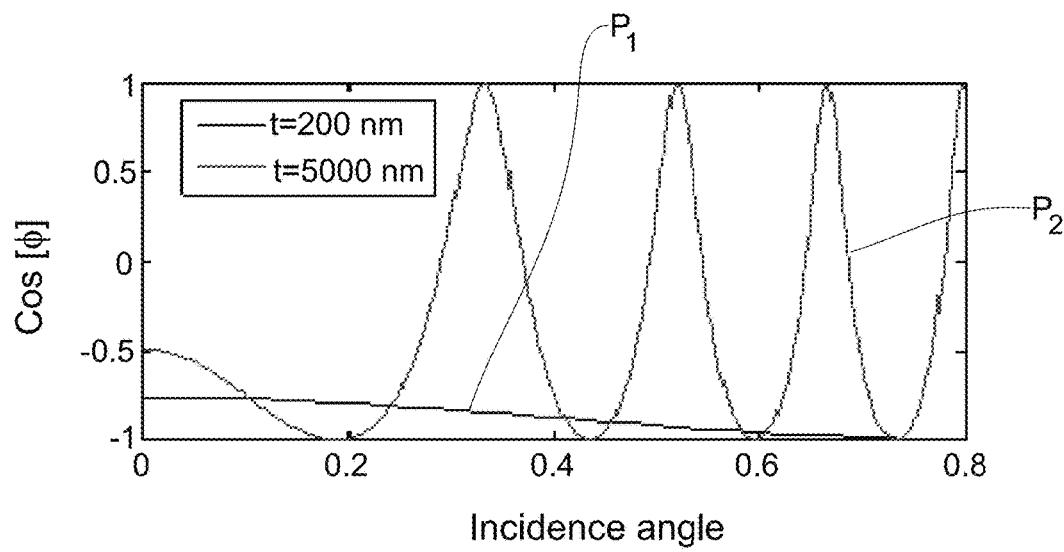
FIG. 9 demonstrates how the technique of the present invention can be used for measuring in samples with thick films, showing the angular phase dependence on the incident angle for two simple thick-film examples.

The technique of the invention can also be used for thick-layer applications. Angular phase information is specifically rich for applications characterized by large thicknesses. As a simple example, let us consider a trivial thick film deposited over a substrate. Referring to FIG. 9, there are illustrated graphs $P_1$ and $P_2$ of the cosine of the angular phase dependence on the incident angle for two simple examples of SiO2 film of 200 nm and 5000 nm thicknesses deposited on a Si substrate, corresponding to measurements using the technique of the invention with illumination wavelength of 500 nm. As shown in the figure, the phase has weak dependence on the incidence angle for the thinner film example. However, for the thick layer, the phase presents strong dependence on the incidence angle. For such samples, angular phase measurements are especially sensitive to the application parameters. Examples for such applications of importance are shallow trench isolation (STI) and vertical NAND (VNAND) gate. Angular phase metrology of the invention provides a uniquely beneficial approach for the exceptional challenge posed to OCD metrology.

A crucial aspect of any OCD technique is an accurate and efficient algorithmic and modeling capability, which would allow interpretation of the calculated information. The potentially large amount of information provided by angular phase measurements allows for new approaches in the data analysis and compilation. One example for such new methodology deals with the situation when the measured data includes a 2D or 3D information set. As described above, examples for 2D datasets are angular phase measurements obtained for a range of incident angles and azimuths, or over a range of incident angles and wavelengths. 3D datasets can be obtained for example if the angular phase is measured over a range of incident angles, azimuths and wavelengths. While it may be possible to use standard OCD methodology to find the 'best fit' solution to the entire dataset, in these situations such approach may be grossly inadequate or non-optimal. Two issues demonstrating why such a 'simplistic' fitting methodology will be ill-suited are calculation time, and noise reduction.

Considering calculation time, the effort required to calculate the reflection from a multitude of angles and wavelengths poses a challenging task, even considering today's high power computing and advanced algorithms. For OCD, the calculation of a single reflected signal has to be repeated multiple times, in order to find the set of geometrical and\or material properties which would give rise to the measured signal. In this case, it is highly desirable to reduce the number of calculated points.

Such reduction can be obtained in several ways. Specifically, for the case of 2D dataset (which is not common to standard OCD metrology), a host of algorithmic tools can be used borrowed from image processing. Using such tools, a full 2D (or 3D) image can be accurately reproduced using a small set of calculated points. Examples are compressed sensing techniques, neural network methodologies, etc. In practice, a small set of points can be calculated in the 2D\3D space of incident directions\wavelengths\polarizations etc., from which the full dependence can be deduced. Then, the reproduced dataset is compared to the measurement.

It is furthermore possible to select the calculated points based on algorithmic guidelines. Such selection tools have been extensively analyzed and developed, e.g. in the field of compressed sensing [Y. C. Eldar and G. Kutyniok, *Compressed Sensing, Theory and Applications*, Cambridge University Press (2012)]. These tools can indicate which smallest set of calculated points are needed, to accurately map the full measured span of parameters.

As stated, there is another aspect by which a simplistic comparison of the full measured data with a calculation may be non-optimized. It is often beneficial to use over-sampled data to average-out unwanted noise effects. Again, the most common example for such use comes from image processing techniques. For most standard OCD metrology, such noise reduction is limited in benefit, as the acquired information (a 1D spectrum) has little redundancy. For angular phase measurements, when significantly richer information is obtained, it is possible to reduce the amount of information, on account of eliminating noise effects. Examples for such methods are local averaging, low-pass filtration, excursion identification or weighting between measured points according to local noise.

Another approach improving robustness to noise is dimensional reduction of the measured data using for example basis transformation or neural-network projection. In these methods, the full-dimensional measured dataset is converted into a lower dimension representation. This different representation highlights sensitivity to the parameters of interest while reducing sensitivity to noise. In practice, the conversion can take into account known noise models, to specifically eliminate their influence on the measurement.

Another important aspect in obtaining a beneficial fit between measurement and calculation is the correct choice of compared quantities. Angular phase measurements provide additional degrees of freedom in optimizing the fitting process.

The fitting process commonly involves defining a 'merit function', which measured the degree of fit between calculated and measured signals. For standard spectral information, this merit function MF may be the RMS error between measurement and calculation, $$MF = \frac{1}{N}\Sigma_{\lambda,p,\Omega}[I_{Calc}^{\lambda,p,\Omega} - I_{meas}^{\lambda,p,\Omega}]^2. \quad (1)$$

Here, $I_{Calc}^{\lambda,p,\Omega}$, $I_{Meas}^{\lambda,p,\Omega}$ are the calculated and measured reflected intensities, for the measured wavelengths $\lambda$, polarizations p and incident\reflected angles $\Omega$, and N is the number of data points under comparison.

However, when angular phase is measured, there is additional flexibility in defining the merit function. One example is to simply use the RMS error between both intensity I and phase $\phi$ simultaneously, $$MF = \frac{1}{N}\Sigma_{\lambda,p,\Omega}[I_{Calc}^{\lambda,p,\Omega} - I_{meas}^{\lambda,p,\Omega}]^2 + [\phi_{Calc}^{\lambda,p,\Omega} - \phi_{meas}^{\lambda,p,\Omega}]^2. \quad (2)$$

However, another possibility is to define the merit function MF as the RMS between the complex fields, rather than intensity and phase. Yet another example for possible merit function MF is the RMS error between the reflected complex electric fields E, $$MF = \frac{1}{N}\Sigma_{\lambda,p,\Omega}\left|E_{Calc}^{\lambda,p,\Omega} - E_{meas}^{\lambda,p,\Omega}\right|^2. \quad (3)$$

As the relation between these variations is not linear, they have different sensitivity to different noise factors.

It should be understood that the above represent only a small set of examples. In practice, the amount of information obtained by angular phase metrology allows for diverse variations of MF definitions.

Thus, the present invention provides a novel technique, based on angular phase measurements, for use in measuring in multi-layer structures such as semiconductor wafers, particularly useful for OCD measurements. As indicated above, the angular phase measurements may be implemented to provide 2D information set (e.g. angular phase measurements obtained for a range of incident angles and azimuths, or over a range of incident angles and wavelengths), as well as 3D information set 3D (e.g. the angular phase is measured over a range of incident angles, azimuths and wavelengths).

The invention claimed is:

1. A metrology system for measuring parameters of a structure, the metrology system being configured for performing Optical Critical Dimension (OCD) measurements and comprising:
    an optical system configured for detecting light reflection of incident radiation from the structure and generating measured data indicative of angular phase of the detected light components corresponding to reflections of illuminating light components having different angles of incidence, wherein the optical system comprises imaging and focusing lenses configured to create an image of a pupil of the optical system on a phase detector, thereby providing the measured data indicative of a two-dimensional phase map of the pupil, and
    a control unit configured for receiving and processing the measured data and generating a corresponding two-dimensional phase map of the pupil indicative of variation of the phase along at least one axis of two dimensions used in the two-dimensional phase map, analyzing the two-dimensional phase map and determining one or more parameters of the structure.

2. A metrology system according to claim 1, wherein said two-dimensional phase map of the pupil comprises angular dependent data along at least one axis.

3. A metrology system according to claim 1, wherein said two-dimensional phase map of the pupil comprises angular dependent data along one axis and spectral data along other axis.

4. A metrology system according to claim 1, wherein the two-dimensional phase map of the pupil comprises position dependent data along the two axes.

5. A metrology system according to claim 4, wherein said optical system is configured and operable for illuminating the structure with one or more wavelengths, and detecting the light reflection for said one or more wavelengths.

6. A metrology system according to claim 1, wherein said optical system is configured and operable for illuminating the structure with one or more wavelengths, and detecting the light reflection for said one or more wavelengths.

7. A metrology system according to claim 6, wherein said optical system is configured and operable for illuminating the structure with multiple wavelengths, either concurrently or sequentially.

8. A metrology system according to claim 1, wherein the optical system is configured for implementing one or more polarization schemes, for illuminating the structure with light of a specific polarization, and detecting reflected light of desired polarization, such that the angular phase in the measured data is a function of polarization.

9. A metrology system according to claim 1, further comprising an imaging channel.

10. A metrology system according to claim 9, wherein said imaging channel comprises at least one of imaging and focusing lenses.

11. A metrology system according to claim 1, wherein the optical system comprises a cylindrical lens.

12. A method for use in Optical Critical Dimension (OCD) measurements of one or more parameters of a structure, the method comprising:
performing measurements on the structure, the measurements comprising collecting reflections of illuminating light components having different angles of incidence onto the structure, via a pupil of an optical system, and creating an image of the pupil on a phase detector, thereby providing measured data corresponding to a phase map of the pupil indicative of variation of the phase along at least two dimensions, and
analyzing the phase map and determining one or more parameters of the structure.

13. A method of claim 12, wherein said structure is a multi-layer structure.

14. A method of claim 12, wherein said structure is a semiconductor wafer.

15. A method of claim 14, wherein said one or more parameters of the structure comprise one or more of the following: critical dimensions (CD), side wall angle (SWA), thicknesses, refractive indices.

16. A method of claim 12, wherein said one or more parameters of the structure comprise one or more of the following: critical dimensions (CD), side wall angle (SWA), thicknesses, refractive indices.

17. A method of claim 12, wherein at least one of illuminating the structure with the illuminating light and collecting the reflections of the illuminating light is performed with a specific polarization of the respective light, such that the measured data are a function of polarization.

18. A method of claim 17, wherein said illuminating light comprises one or more wavelengths, and said collecting of the light reflection is performed for said one or more wavelengths.

19. A method of claim 12, wherein said illuminating light comprises one or more wavelengths, and said collecting of the light reflection is performed for said one or more wavelengths.

20. A method of claim 12, wherein said analyzing of the phase map and determining the one or more parameters of the structure include applying a Neural Network Technique.

* * * * *